United States Patent [19]

Baird

[11] Patent Number: 4,748,109
[45] Date of Patent: May 31, 1988

[54] ASSAY METHOD AND REAGENT TO DETERMINE ANTIBODIES TO PAPILLOMAVIRUS VIRIONS

[76] Inventor: Phillip J. Baird, 2 Torrens Place, Cherrybrook, New South Wales 2120, Australia

[21] Appl. No.: 626,777

[22] Filed: Jul. 2, 1984

[30] Foreign Application Priority Data

Jul. 1, 1983 [AU] Australia ................ PG0083

[51] Int. Cl.$^4$ ............... G01N 33/543; G01N 33/544; G01N 33/569; G01N 33/574
[52] U.S. Cl. ........................... 435/5; 435/7; 435/28; 436/518; 436/527; 436/531; 436/813
[58] Field of Search ............. 436/64, 813, 527, 529, 436/531, 532, 534, 548; 435/57, 235; 530/826

[56] References Cited

U.S. PATENT DOCUMENTS

4,024,235  5/1977  Weetall ........................ 436/508
4,315,907  2/1982  Fridlender .................... 435/7

FOREIGN PATENT DOCUMENTS

8202774  8/1982  PCT Int'l Appl. ............... 435/7

OTHER PUBLICATIONS

L. Gissmann et al., *Proc. Nat. Acad. Sci. U.S.A.*, 73, 1310–1313, 1976.
L. Gissmann et al., *Virology*, 76, 569–580, 1977.
H. Pfister et al., *Int. Journ. Cancer* 21, 161–165, 1978.
L. Hudson et al., *Practical Immunology* 2nd ed., Blackwell Scientific Publications, Oxford, pp. 220–225, 237–239, 314–317, 1980.
A. B. Jenson et al., *Journ. Natl. Cancer Inst.* 64, 495–498, 1980.
R. F. LaPorta et al., *Proc. Natl. Acad. Sci. (U.S.A.)* 79, 3393–3397, 1982.
A. Voller *Diagnostic Horizons* 2(1), 1–7, 1978.

*Primary Examiner*—Sidney Marantz
*Assistant Examiner*—David A. Saunders

[57] ABSTRACT

The invention provides a reagent and assay to detect, inter alia anogenital warts, cervical intraepithelial neoplasia and invasive squamous cell carcinoma of the uterine cervix using disrupted *Papillomavirus virions* or antigen extract thereof.

21 Claims, 3 Drawing Sheets

ANTIBODY LEVELS (GEOMETRIC MEAN + SD) FOR CONTROL GROUP AND PATIENTS WITH C.I.N., ANOGENITAL WARTS, AND NON-CERVICAL CANCERS.

Figure 2:
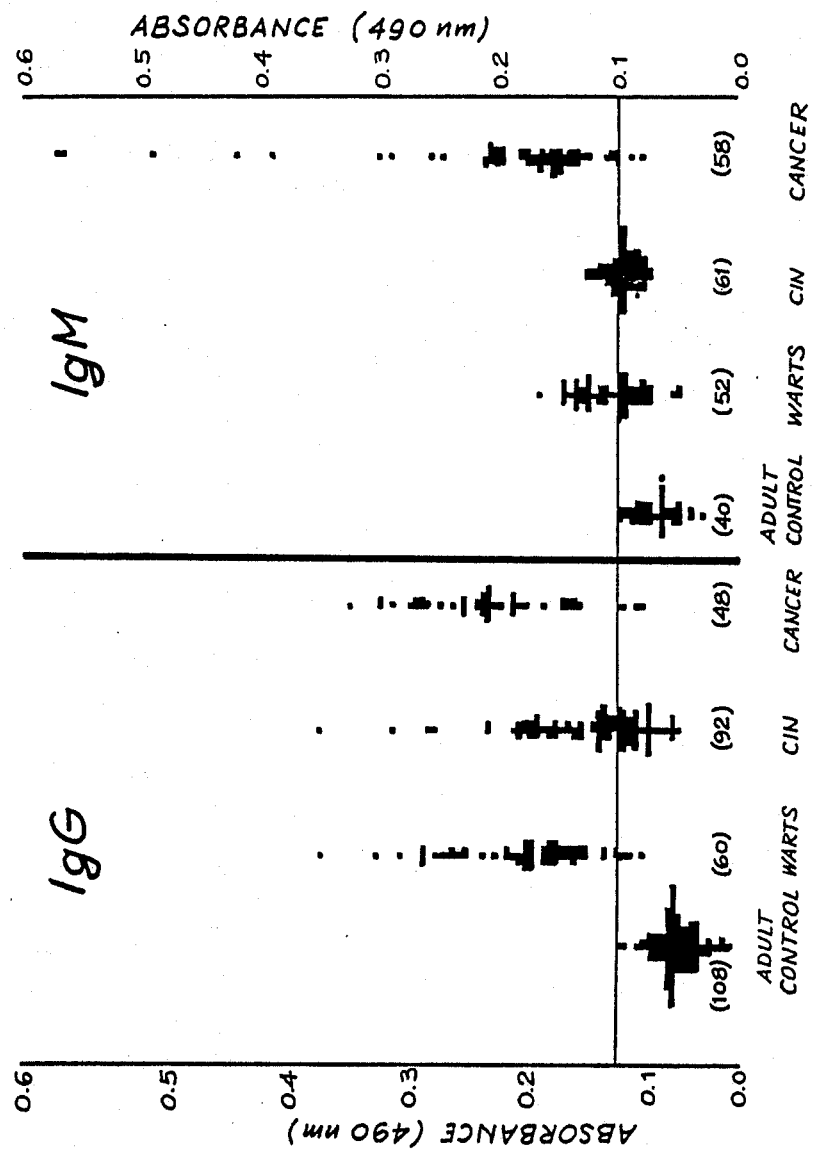

FIG. 2  ANTIBODY LEVELS FOR CONTROL GROUP AND PATIENTS WITH ANOGENITAL WARTS, C.I.N. AND CERVICAL CANCER.

IgM ANTIBODY LEVELS (GEOMETRIC MEAN + SD) FOR CONTROL GROUPS AND PATIENTS WITH ANOGENITAL WARTS, C.I.N., AND CERVICAL CANCER.
(CONTROLS: 1 - ADULT FEMALES, 2 - PATIENS WITH OVARIAN CARCINOMA).

DILUTION of RABBIT ANTI-BPV-SDS IgG

VARIOUS DILUTIONS OF RABBIT ANTI-BPV-IgG (•) AGAINST BPV-SDS ANTIGEN (0.5 ng) COATED ON WELLS OF POLYSTYRENE PLATE. (THE BROKEN LINE DENOTES THE POSITIVE AND NEGATIVE CUT-OFF POINT)

1 : 100 DILUTION OF RABBIT ANTI-BPV-SDS IgG AGAINST BPV-SDS ANTIGEN 0.5 ug COATED ON WELLS OF POLYSTYRENE PLATE INCUBATED FOR VARIOUS PERIODS OF TIME.

ASSAY METHOD AND REAGENT TO DETERMINE ANTIBODIES TO PAPILLOMAVIRUS VIRIONS

The present invention relates in particular to a reagent for, and a method of, identifying mammals such as humans with inter alia, anogenital warts, cervical intraepithelial neoplasia (CIN) and invasive squamous cell carcinoma of the uterine cervix. The invention is based on the discovery by the present inventor that levels of antibody to a group specific Papillomavirus antigen are raised in the sera of patients with anogenital warts, CIN and cervical squamous carcinoma.

The methods now used for detecting the above conditions generally utilise cell sampling techniques. The ability to detect the disorders by means of serum or other body fluid assays provides a more sensitive method of detecting same and gives rise to the possibility of mass screening for such disorders.

In one form the present invention provides a reagent useful in the detection of anogenital warts, CIN or cervical squamous carcinoma, comprising a solid or particulate support coated with proteins of disrupted Papillomavirus virions, or antigen extract thereof.

In another form the invention provides a method for preparing a diagnostic reagent useful in the detection of anogenital warts, CIN and cervical squamous carcinoma, said method comprising the steps of:

(i) contacting a solid or particulate support with disrupted Papillomavirus virions or antigen extract thereof;

(ii) incubating said support with said virions or extract for a time and at a temperature suitable for proteins of said virions or extract to adhere to said support; and (iii) removing excess virions which have not adhered to said incubated support.

In another form the invention provides a method for the detection of anogenital warts, cervical intraepithelial neoplasia (CIN) and invasive squamous carcinoma of the uterine cervix, said method comprising the steps of:

(1) providing a solid or particulate support coated with proteins of disrupted Papillomavirus virions or an antigen extract thereof;

(2) contacting said coated support with an aliquot of a body fluid under suitable conditions so as to form a complex between proteins of said virions or antigen extract thereof and antibodies in said aliquot, and (3) detecting quantitatively or qualitatively the presence of said complex.

The invention also provides a kit useful in an assay as described above, said kit including:

(i) a diagnostic reagent as described herein; and
(ii) one or more aliquots of anti IgG and/or anti IgM.

Preferably the virions are human or bovine virions, such as bovine Papillomavirus type 2 (BPV-2) virions. In an alternative form of the invention, the Papillomavirus virions may be replaced by the Papillomavirus antigen extract purified therefrom.

It is well recognised that human Papillomavirus (HPV) consists of a heterogeneous group of viruses which, while morphologically similar, are distinct in their DNA restriction enzyme cleavage patterns and the antigenicity of their capsid proteins. Furthermore, each HPV sub-type is generally characterized by topographical and histological variations; for example, HPV-1 and plantar warts; HPV-6 and condyloma acuminatum. The use of the term Papillomavirus embraces each sub-type or a mixture of one or more of the sub-types, as each subtype is considered to be useful in the methodology of the present invention.

In one preferred form of the invention, the virions are bovine Papillomavirus type 2 (BPV-2) virions. These virions preferably are prepared from bovine neck fibropapillomas by procedures known to those skilled in the art. However, other papillomas may be used as the source of the virus particle, for example, from humans, rabbits or horses. A preferred methodology is that described by La Porta R. F. and Taichman L. B.; 1982, Proc. Nat. Acad. Science U.S.A. 79, 3393–3397. The virions are disrupted, preferably by mechanical means or by contact with a surfactant, detergent or high salt concentration such as with sodium dodecylsulfate. Preferably the virions are disrupted by the method described in Jenson A. B. et al, 1980; J. Nat. Cancer Instit. 64, 495–500. Preferably the disrupted virions are contacted with a detergent as well as mercaptoethanol, or the like, to maintain the proteins thereof in an "open" configuration.

If desired, the virions may be further purified to obtain various antigenic fractions, for example by preparative PAGE or by sucruse gradient centrifugation (5–15% wt/v), and the appropriate antigen fractions identified and used.

In a preferred embodiment of the invention, the support is a solid support, preferably a water insoluble polymeric material such as polypropylene, polystyrene, polycarbonate, polyethylene or polyamide. The surface of the support may be derivatised to promote binding or absorption. Alternatively, the support may be glass, preferably which has been appropriately treated to promote adsorption of the virions to the glass surface. Alternatively the support may be a particulate support such as sepharose or latex particles. The disrupted virions are incubated with the support for sufficient time for them to be adsorbed on or bind to the support, preferably about 12 to 24 hours at about 4° C. The coated support is then washed to remove excess virions.

The washed, coated support is then contacted with an aliquot of body fluid such as whole serum or a serum fraction which may be diluted. The fluid is incubated with the coated support for an appropriate time such as 1 to 20 hours at a temperature range of from 4° C. to 45° C., preferably 25°–35° C., so as to form a complex between the papilloma virus (PV) antigen(s) on said support and the antibodies in the fluid if present.

Although it would be clear that the complex may be detected by a number of methods, the complex is most preferably detected by enzyme linked immunosorbent assay (ELISA). For example, the complex is contacted with peroxidase conjugated anti human IgG, such as peroxidase conjugated rabbit anti-human IgG, and incubated therewith for a sufficient period of time and under suitable conditions so that said anti IgG binds to said complex. The extent of bound, peroxidase-conjugated anti human IgG may be determined spectrophotometrically at 490 nm using o-phenylenediamine.

Alternatively, the complex may be detected by radioisotope techniques using radio labelled reagents specific for the complex, e.g. $I^{125}$ labelled monoclonal or polyclonal antibodies.

In one form of the diagnostic method, the body fluid comprises a serum fraction from which IgG immunoglobulins have been removed. This may be obtained by passing whole serum through an appropriate separation column (Quik-Sep, from Isolab, Ohio).

The incubation time of the non-IgG serum fraction with the coated support is increased to about 16 hours as compared to the preferred time of about 2 hours for the serum containing IgG immunoglobulins. The reagent for the detection of the PV anitgen-antibody complex is preferably an anti IgM antibody, or anti IgA antibody, most preferably peroxidase conjugated.

It has been found that the difference in quantitative results achieved from assays of a body fluid containing IgG immunoglobulins followed by detection of the IgG complex, and assays of a non IgG serum fraction followed by detection of a non IgG complex, such as IgM or IgA complex, may provide useful results. It has been found that both cancer, pre cancer and patients with warts have high IgG levels. The IgG based assay does not discriminate for cancer patients. However, the IgM assay indicates a high level of IgM in patients with cancer compared to patients with warts or pre cancer of the cervix. For example; patients with warts, 55% positive; pre cancer patients, 29% positive; and, cancer patients, 90% - positive using a cut off level of the mean plus 3 standard deviations of the control group. However, if the cut off is mean plus 2 standard deviations of the wart group then the positive rate would be 0% for the wart group and pre cancer group, and 67% for the cancer group. A combination of the IgG and IgM results could be diagnostic of carcinoma of the cervix. This could also be useful in assaying patients post treatment to determine whether there is any recurrence of the condition.

Therefore, one possible use of the present invention could be to monitor patients after treatment to detect early recurrences of tumor so that second line treatment can be instituted or the invention can be used to select out patients who have been cured by one form of treatment and so spare them the effects of additional surgery and/or radiation treatment.

A preferred form of the invention will now be described with reference to the following Examples and drawings wherein FIGS. 1 to 6 graph the results obtained in the Examples and will be described in conjunction therewith.

EXAMPLE 1

All patients had 10 ml of blood collected before treatment or at the time of diagnosis. The serum was separated and stored at −20° C. Study groups were patients with anogential warts (60), CIN (92), and cervical cancer (46). All those with CIN or cancer had their diagnoses confirmed by routine histopathological examination of punch biopsy material. The control groups consisted of: (1) 16 babies aged six to eighteen months, 16 children aged 6 years, and 16 children aged 12 years; (2) 108 symptom-free, non-hospital females aged 20–60 years; (3) 60 females aged 15–40 years seen at sexually transmitted disease clinics; and (4) 40 females with non-cervical upper genital tract cancers.

PREPARATION OF REAGENT

Bovine papillomavirus type 2 (BPV-2) virions were prepared from bovine neck fibropapillomas. The keratin was scraped from the lesions, ground with mortar and pestle, and subjected to differential ultracentrifugation including trichlorotrifluoethene lipid extraction. The final pellet was prepared from the virus band seen on a cesium chloride gradient. The virions were disrupted in 1% sodium dodecylsulphate and 2% mercaptoethanol, diluted in phosphate-buffered saline pH 7.6 and adjusted to a final protein concentration of 1.25 mg/ml. The disrupted virions were coated onto polystyrene plates and incubated overnight at 4° C. After washing with buffer or physiological saline they were ready for use.

ASSAY PROCEDURE 100 ul of 1:100 diluted whole serum was added to each plate for a 2 h incubation at 37° C. After several further washes, 100 $\mu$l of 1:500 peroxidase conjugated rabbit anti-human IgG was added, for a 2 h incubation at 37° C. Then 100 ul of o-phenylenediamine (OPD) (4 ml of 1% stock OPD in methanol to 96 ml of 0.15 M citric phosphate buffer pH 5.0 with 40 $\mu$l of 30% $H_2O_2$)---, was added and the reaction was stopped by addition of 500 $\mu$l of 5 mol/l sulphuric acid. The colour intensity was determined at 490 nm with a Dynatech spectrophotometer. All sera were assayed in duplicate and those showing more than 10% difference were reassayed.

RESULTS

The specificity of the assay was tested with several reagent blanks, negative sera from children aged six to twelve months, and whole virions (as negative antigen). A positive control serum was obtained from rabbits previously injected with disrupted virions. All negative control experiments gave readings less than or equivalent to that of the reagent blank.

The sensitivity of the assay was determined with varying dilutions of antigen and antibody over various time intervals. Overnight incubation gave the highest reading. Serum dilutions of 1:1600 were still detectable above background readings. With a fixed dilution (1:100) of positive control serum, as little as 0.15 $\mu$g of antigen per well was detectable above background readings. The reproducibility of the assay was determined by within-assay and between-assay variation coefficients. Forty sera with absorbance readings ranging from 0 to 0.40 were used. The within-assay coefficient of variation was 4.1% and the between-assay coefficient of variation was 4.8%.

The assay was then applied to the analysis of sera from patients with anogenital warts, CIN, and cervical cancer. All tests were done at a fixed antigen concentration (0.4 $\mu$g/well) and a fixed serum dilution (1:100). In this study, the mean value of the children's sera plus 3 standard deviations above was accepted as a cut-off level (99% confidence) for a positive result. Thus, 8.3% of symptomless females aged 20–60 years had antibody to the group specific antigen; 100% of patients with skin or anogenital warts had antibody. However, for analysis of the cancer data, the mean value plus 3 standard deviations of the non-selected symptomless adult controls (group 2) was accepted as a cut-off point for a negative or positive result. Thus, 6.6% of a sexually active population (control group 3) were positive, as were 15% of a group with non-cervical cancer. However, in patients with anogenital warts, CIN, and cervical cancer the proportions with positive results were 95%, 60%, and 93%, respectively, as shown in Table 1.

TABLE 1
PERCENTAGE POSITIVITY FOR SERA FROM CONTROL AND STUDY GROUPS

| | Age (yr) Mean ± SD | Range | No. | No positive (%) |
|---|---|---|---|---|
| Subjects | | | | |
| Controls: | | | | |
| 1. Children | — | 0.5–12 | 48 | 0 (0) |
| 2. Adults | 38 ± 15 | 20–60 | 108 | 0 (0) |
| 3. STD clinic | 31 ± 10 | 20–45 | 60 | 4 (6.6) |
| 4. Non-cervical cancer | 55 ± 12 | 35–60 | 40 | 6 (15.0) |
| Anogenital warts | 34 ± 11 | 17–70 | 60 | 57 (95) |
| Cervical intraepithelial neoplasia | 29 ± 7 | 19–52 | 92 | 55 (60) |
| Cervical cancer | 52 ± 16 | 29–83 | 46 | 43 (93) |

Figure 1:
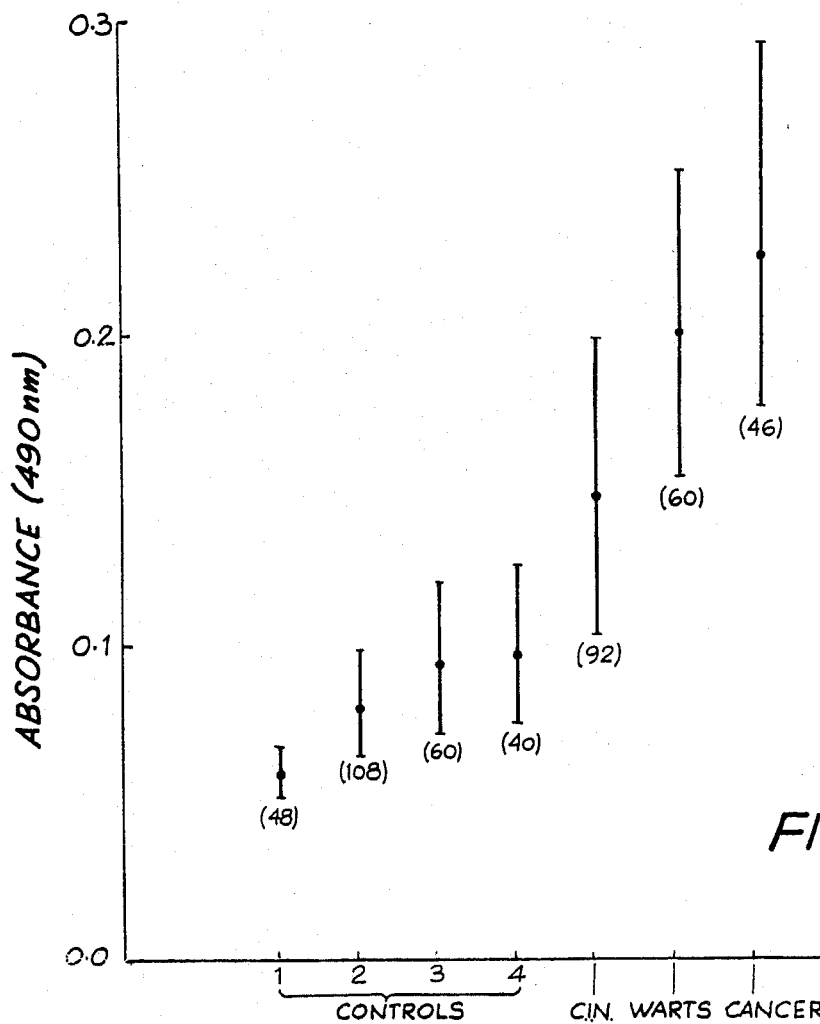

Viewed quantitatively, as shown in FIG. 1, the level of antibody in the cancer group differs very significantly ($p<0.001$) from that in all other groups except the patients with anogenital warts ($0.01<p<0.02$). Similarly, the values for the anogenital warts and CIN groups differed very significantly ($p<0.001$) from those in all the control groups.

EXAMPLE 2

Patients

The study groups were patients with anogenital warts (51), CIN (61) and cervical cancer (54). All the CIN and cancer cases had the diagnoses confirmed by routine histopathology and punch biopsy material. The control groups consisted of:

1. asymptomatic non hospital female adults, aged 20–60 years (40),
2. females with non cervical upper genital tract cancers (10).

ANTIGEN AND ASSAY

The antigen was identical to that described in Example 1. The assay was also similar except that the patient's serum was diluted 1:50 and was incubated at 25° C. for 16 hours with the anitgen. Prior to this step, the whole serum sample had been passed through a Quik-Sep IgM isolation column (Iso-Lab, Ohio, U.S.A.) to remove the IgG fractions. After incubation of the human serum fraction with the antigen, 100 $\mu$l of 1:500 peroxidase conjugated rabbit anti-human IgM was added, instead of anti-human IgG.

RESULTS

Figure 3:
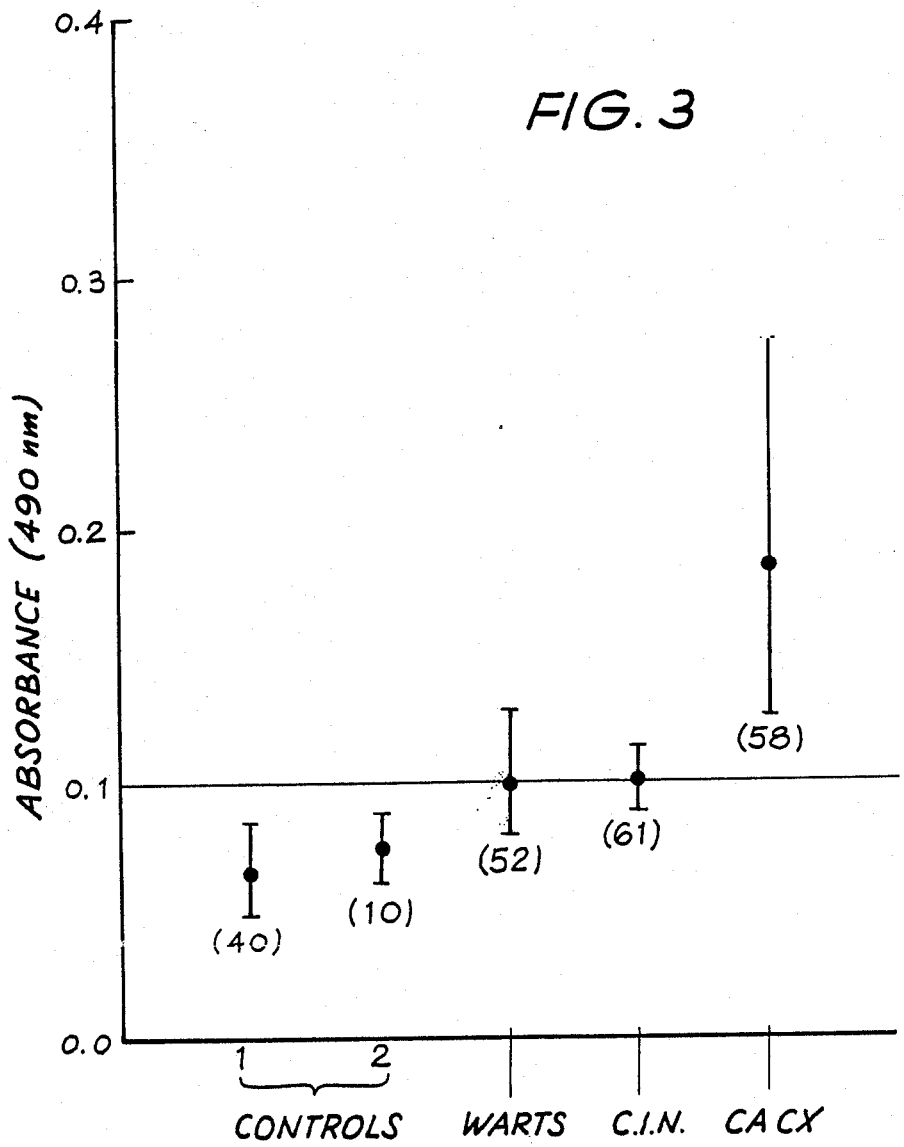

The means optical density (O.D.) of each group was compared as shown in FIG. 3. Experiments (n=12) for IgM isolation gave a recovery of 76% on average. In 80% of the samples assayed, IgG was not detectable by nephelometry in the IgM fraction. The use of the Quik-Sep isolation columns also eliminated the possibility of cross reactions with serum rheumatoid factor.

The assay was then applied to the study of IgM levels in both the control and study groups. FIG. 2 compares the O.D. readings for the assay results of Example 1 (IgG) and the assay results of Example 2 (IgM). The cut off level for a positive or negative result was calculated from the mean plus 3×SD above the mean of the control groups. The control groups, as indicated in FIGS. 2 and 3 showed very low levels consistent with the reagent blank readings.

However 54% of the patients with anogenital warts, 29% of patients with CIN and 95% of patients with invasive cervical carcinoma were positive for elevated IgM to group specific PV antigen(s) (Table 2). When viewed quantitatively as shown in FIG. 3, the cancer group had highly significant IgM levels ($p<0.001$) compared to the control groups and the other study groups. There was no significant difference between the wart and CIN groups. These, however, were significantly different from the control groups ($p<0.001$).

TABLE 2
PERCENTAGE POSITIVITY FOR SERA FROM CONTROL AND STUDY GROUPS

| | Age (yr) Mean ± SD | Range | No. | No positive (%) |
|---|---|---|---|---|
| Subjects | | | | |
| Controls: | | | | |
| 1. Adult females | 38 ± 15 | 20–60 | 40 | 0 (0) |
| 2. Ovarian carcinoma | 55 ± 12 | 45– | 10 | 0 (0) |
| Anogenital warts | 34 ± 11 | 17–70 | 52 | 28 (54) |
| Cervical intraepithelial neoplasia | 29 ± 7 | 19–52 | 61 | 18 (29) |
| Cervical cancer | 52 ± 16 | 29–83 | 58 | 55 (95) |

EXAMPLE 3

Papillomavirus Antigen And Antiserum:

Papillomavirus virions were prepared and purified from fresh bovine cutaneous fibropapillomas. The viral particles were disrupted after addition of sodium dodecylsulfate and $\beta$-mercaptoethanol to a 1% w/v and 2% v/v concentration respectively, and the viral suspension was boiled for one minute. The protein content of the antigen (BPV-SDS), as determined by the Lowry's method (1951), was 1.5 mg/ml. Antiserum was prepared from rabbits immunized with the antigen in both complete and incomplete Freund's adjuvant. The IgG fraction of the rabbit serum was isolated by DEAE Affi-Gel Blue chromatography (Bio-Rad Laboratories). Flat-bottom-well polystyrene plates (Dynatech) were washed with double distilled water. The wells were coated with 100 ul of the BPV-SDS antigen (0.5 $\mu$g/well) diluted in 0.06 M carbonate-bicarbonate buffer Ph 9.6. Plates were put inside closed plastic bags with moist cotton and incubated at 4° C. for 16 h. They were then washed three times with phosphate-buffered saline pH 7.4, containing 0.05% Tween-20 nonionic surfactant (PBS-T20).

HUMAN SERUM

Human sera were collected from 16 babies and 31 children ages six months to 12 years, 108 adults without clinically apparent warts, and 60 patients with skin warts and genital warts. Care was taken to avoid hemolysis and bacterial contamination. All sera were stored at $-20°$ C. until used.

ASSAY

100 $\mu$l of human serum, diluted 1:100 (or two fold dilution of rabbit anti-BPV-SDS IgG) in diluent buffer pH 7.4 (0.05 M Tris-HCL, 1.0 mM MgCl$_2$, 0.15 M NaCl, 0.05% T20 and 1% bovine albumin w/v) were then added to the wells and incubated at 37° for 2h. After three more washes with PBS-T20, 100 $\mu$l of 1:800 dilution of peroxidase conjugated rabbit anti-human IgG in diluent buffer (or peroxidase conjugated swine anti-rabbit IgG, DAKO, Copehagen, Denmark) was added to each well. The plates were again incubated at 37° C. for 2h. Following further washing, 100 $\mu$l of O-phenylenediamine (OPD) (4 ml of 1% stock OPD in methanol to 96 ml of 0.15 M citric phosptate buffer pH 5.0 with 40 μl of 30% $H_2O_2$) was added to each well. After 40 minutes incubation at room temperature in the dark, the reactions were stopped by adding 30 μl of 5 N $H_2SO_4$. The colour intensity was determined at 490 nm in a Dynatech spectrophotometer. All reagents used in the assay were sterilized and filtered by 0.45 nm-pore size membrane filters.

RESULTS

Specificity Of Rabbit Anti-BPV-SDS IgG To BPV-SDS Antigen

Figure 4:
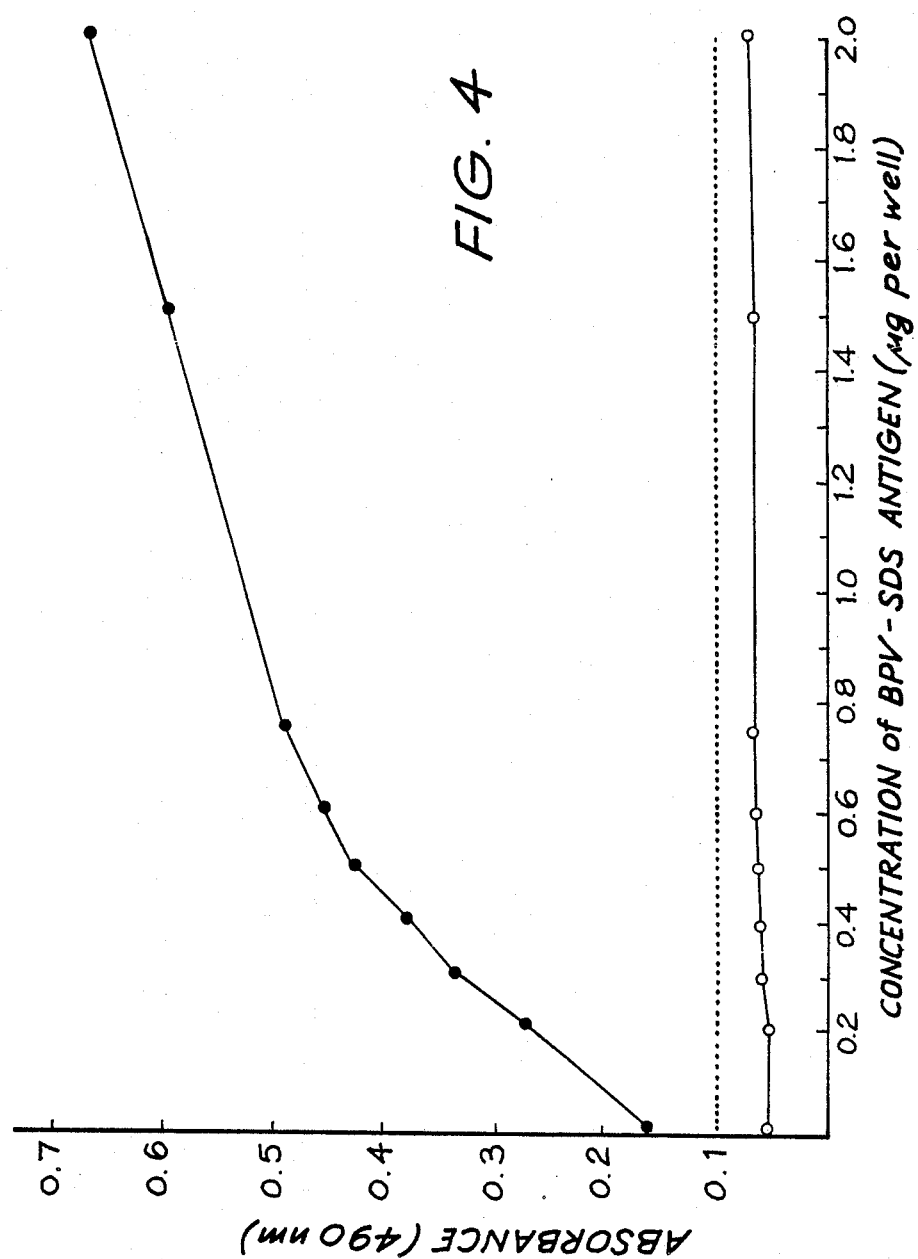

Various concentrations of BPV-SDS antigen (0.15–2.00 μg) or intact BPV virions were coated on wells of a polystyrene plate and incubated with a 1:100 dilution of rabbit anti-BPV-SDS IgG. FIG. 4 shows that rabbit anti-BPV-SDS IgG did react with BPV-SDS antigen, and the absorbance was proportional to the amount of the antigen coated on the wells. In addition, FIG. 4 illustrates that concentrations of antigen as low as 0.15 μg/well still react with the rabbit IgG. The results demonstrate that the assay is highly specific and sensitive.

Figure 5:
Figure 6:
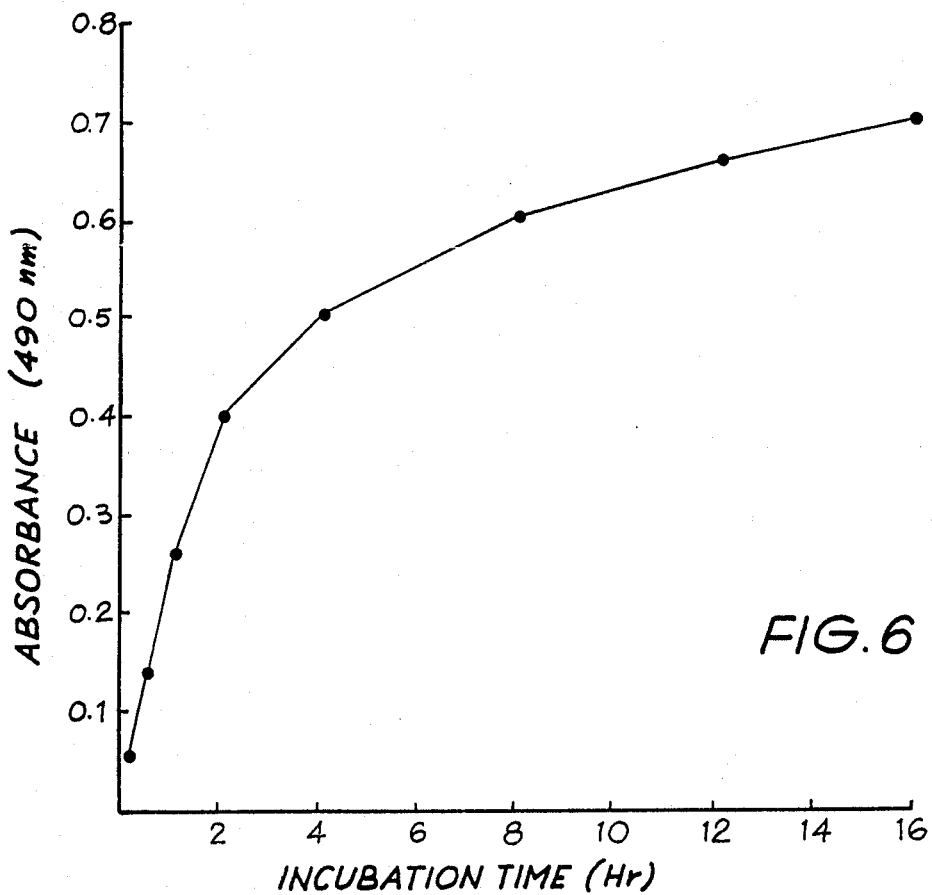

The SENSITIVITY of the assay was determined by adding various dilutions of rabbit IgG to a fixed amount of BPV-SDS antigen (0.5 ug) coated on the wells of a polystyrene plate. Dilutions as low as 1:1600 of rabbit anti-BPV-SDS IgG still gave readings above background values. (FIG. 5).

The REACTION RATE of specific rabbit IgG to BPV-SDS antigen was examined (FIG. 6). 0.5 μg of BPV-SDS antigen was coated onto wells of a polystyrene plate and incubated with 1:100 dilution of rabbit anti-BPV-SDS IgG for various periods of time. The reaction rate was approximately linear over the incubation interval of 1–16 hour. The longer incubations gave the highest O.D. reading. The effect of different incubation temperatures was also studied with 37° C. giving the better results. Control experiments were established to detect any non-specific reactivity in the ELISA procedure. A known positive and negative serum were used as controls in each series of tests. Also the positive serum alone without viral antigen was tested as to whether when absorbed to adsorb to the wells, it reacted with the peroxidase conjugated anti-serum or the substrate. Additionally the antigen alone was tested against the secondary antibody and the substrate. Finally specific rabbit IgG was tested against intact BPV virions. All of the above control situations gave negative results readings equal to background levels of reactivity.

What I claim is

1. A reagent useful in the detection of anogenital warts, cervical intraepithelial neoplasia and cervical squamous carcinoma, said reagent comprising a solid or particulate support coated with proteins of disrupted Papillomavirus virions, or antigen extract thereof.

2. The reagent of claim 1 wherein said support is selected from the group consisting of: polyethylene, glass, polystyrene, polypropylene, polycarbonate, polyamide, and polyacrylic acid.

3. The reagent of claim 1 or 2 wherein said Papillomavirus virions are bovine, human, rabbit or horse papillomavirus virions or antigen extract thereof.

4. The reagent of claim 1 wherin said virions are prepared by grinding papillomas, isolating the virus particles and treating said particles with a surfactant or effective salt concentration to disrupt them.

5. The reagent of claim 4 wherein said surfactant is sodium dodecyl sulfate.

6. The reagent of claim 4 wherein the virions are treated with sodium dodecyl sulfate and/or mercaptoethanol.

7. A method for preparing a diagnostic reagent useful in the detection of anogenital warts, cervical intraepithelial neoplasia and cervical squamous carcinoma, said method comprising the steps of;
    (1) contacting a solid particulate support with disrupted Papillomavirus virions or an antigen extract thereof;
    (2) incubating said support with said virions or extract for a time and at a temperature suitable for proteins of said virions or extract to be absorbed to or bind to said support; and
    (3) removing excess virions or extract which had not adhered to said incubated support.

8. The method of claim 7 wherein said solid or particulate support is polyethylene, glass, polystyrene, polypropylene, polycarbonate, polyamide, or polyacrylic acid.

9. The method of claim 7 or 8 wherein said disrupted Papillomavirus virions are derived from bovine papilloma cells.

10. The method of claim 7 wherein the virions are extracted from papilloma cells by mechanical means, the virus particles isolated, and said particles are disrupted by contact with a surfactant, detergent or effective salt concentration.

11. The method of claim 10 wherein extraction of said virions from the cells is by differential ultracentrifugation.

12. A method for the detection of anogenital warts, Cervical intraepithelial neoplasia (CIN) and invasive squamous cell carcinoma of the uterine cervix, said method comprising the steps of: (1) providing a solid or particulate support coated with proteins of disrupted Papillomavirus virions or an antigen extract thereof; (2) contacting said coated support with an aliquot of a body fluid under suitable conditions so as to form a complex between the proteins of said virions or antigen extract thereof and antibodies in said aliquot, and (3) detecting quantitatively the presence of said complex.

13. The method of claim 12 wherein step (3) comprises the steps of: (i) washing said coated support to remove excess body fluid, (ii) contacting said coated support after washing with an enzyme conjugated antibody capable of binding to said complex formed in step (2), and (iii) incubating said coated support with said conjugated antibody for a sufficient time and at a temperature suitable for the antibody to bind to said complex; (iv) washing said coated support so as to remove excess unbound conjugated antibody, and (v) detecting quantitatively or qualatively the presence of said enzyme.

14. The method of claim 13 wherein said conjugated antibody is peroxidase conjugated anti-human IgG.

15. The method of claim 13 wherein prior to contact of said body fluid with said reagent, IgG is removed from said body fluid.

16. The method as claimed in claim 13 wherein said antibody is peroxidase conjugated anti-human IgM.

17. The method of claim 12 wherein said support is selected from the group consisting of: polyethylene, glass, polystyrene, polypropylene, polycarbonate, polyamide, and polyacrylic acid.

18. The method of claims 12 or 17 wherein said Papillomavirus virions are bovine, human, rabbit, or horse Papillomavirus virions or antigen extract thereof.

19. The method of claim 12 wherein said virions are prepared by grinding papillomas, isolating the virus particles and treating said particles with a surfactant or effective salt concentration to disrupt them.

20. The method of claim 19 wherein said surfactant is sodium dodecyl sulfate.

21. The method of claim 19 wherein the virions are treated with sodium dodecyl sulfate and/or mercaptoethanol.

* * * * *